United States Patent [19]

Gandour et al.

[11] Patent Number: 5,358,942
[45] Date of Patent: Oct. 25, 1994

[54] INHIBITION OF PROTEIN KINASE C WITH CYCLIC PHOSPHONATE COMPOUNDS

[75] Inventors: Richard D. Gandour; Gnanasambandam Kumaravel, both of Blacksburg, Va.

[73] Assignee: Louisiana State University, Baton Rouge, La.

[21] Appl. No.: 128,340

[22] Filed: Sep. 29, 1993

[51] Int. Cl.$^5$ ................... A61K 31/675; C07F 9/6581
[52] U.S. Cl. ...................................... 514/110; 558/81
[58] Field of Search ........................... 558/81; 514/110

Primary Examiner—Patricia L. Morris
Assistant Examiner—Michael G. Ambrose
Attorney, Agent, or Firm—Richard J. Hammond

[57] ABSTRACT

Compounds of the present invention are those having the formula:

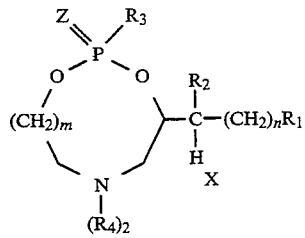

where $R_1$ and $R_3$ are the same or different and are a linear or branched chain of 1 to 22 carbon atoms selected from the group consisting of alkyl, alkenyl or alkynyl or said $C_1$ to $C_{22}$ chains substituted with halo, $-SR_5$, $-OR_5$, $-NHR_5$, $-NR'_5R_5$ or $-C(O)OR_6$ where $R_6$ is hydrogen or $C_1$ to $C_6$ alkyl; $R_5$ and $R'_5$ are the same or different and are hydrogen, amino-alkyl substituted with phenyl, substituted phenyl, benzoyl, substituted benzoyl, heteroaryl or substituted heteroaryl; $R_2$ is hydrogen, $C_1$ to $C_6$ alkyl, phenyl or substituted phenyl; $R_4$ is hydrogen, $C_1$ to $C_6$ alkyl, phenyl or substituted phenyl; Z is sulfur or oxygen; m is an integer from 1 to 3; and n is an integer from 1 to 23.

The compounds provide useful methods of inhibiting protein kinase C.

22 Claims, No Drawings

INHIBITION OF PROTEIN KINASE C WITH CYCLIC PHOSPHONATE COMPOUNDS

FIELD OF INVENTION

The invention relates to novel compounds useful as inhibitors for certain enzymatic-regulated lipid metabolites in eukaryotic cells. Specifically, this invention relates to certain dioxaazaphosphocanes and dioxaazathiophosphocanes and to methods for using such compounds as therapeutic agents.

BACKGROUND OF INVENTION

Hemicholinium related lipids are new synthetic, biologically active compounds. (R. D. Gandour and G. Kumaravel, LSU, U.S. Pat. No. 5,196,418). These compounds inhibit protein kinase C, (G. Kumaravel, C. L. Ashendel and R. D. Gandour, *J. Med. Chem.* 1993, 36, 177) inhibit aggregation of erythrocytes by clusterin or fibrinogen, [I. B. Fritz, K. Burzdy and R. D. Gandour, *Workshop on Clusterin* (Pembroke College, Cambridge, UK, 13-16, September 1992) 21; K. Burdzy, R. D. Gandour and I. B. Fritz, *Workshop on Clusterin* (Pembroke College, Cambridge, UK, 13-16, September 1992) 22] and potently kill sperm and other cells. These cationic lipids structurally resemble the aryl hemicholiniums, which inhibit acetylcholine synthesis by blocking the uptake of choline, [F. C. Macintosh, R. I. Birks and P. B. Sastry, *Nature* (London), 1956, 178, 1181; J. E. Gardiner, *Biochem. J.*, 1961, 81, 297; P. Guynet, J. Bossier, J. Beaujouan and J. Glowinski, *Brain Res.*, 1973, 62, 523; L. A. Smart, *J. Med. Chem.*, 1983, 26, 104] serve as substrates for choline acetyltransferase, [B. Collier, and F. G. Macintosh, *Canad. J. Physiol. Pharmocol.*, 1969, 47, 127; B. A. Hemsworth, *Eur. J. Pharmacol.*, 1971, 15, 91; S. M. Shreeve, G. B. Veitch and B. A. Hemsworth, *J. Med. Chem.*, 1984, 27, 754] and inhibit acetylcholine esterase. [B. H. Lee, T. C. Stelly, W. J. Colucci, J. G. Garcia, R. D, Gandour, and D. M. Quinn, *Chem. Res. Toxicol.*, 1992, 5, 411].

Acyltransferases regulate many steps in the synthesis and the metabolism of lipids. Cells require lipid synthesis to produce components of membranes, and cells employ lipid metabolism as an alternative source of energy to glucose metabolism. Inhibitors of various enzymes in both these pathways find use as potential therapeutic agents or biocides or both. Hemipalmitoyl carnitinium (HPC), structural analogue of hemicholinium lipids, potently inhibits carnitine palmitoyltransferase (CPT), [Gandour, R. D. Leung, O. -t.; Greway, A. T.; Ramsay, R. R.; Nic a' Rhaird, N.; Fronczek, F. R.; Bellard, B, M.; Kumaravel, G., *J. Med. Chem.*, 1993, 35, 237–242] which many believe is the rate-limiting step for hepatic mitochondrial β-oxidation of long-chain fatty acids. CPT activity usually increases under certain conditions, e.g., starvation and diabetes, resulting in higher levels of fatty-acid oxidation and ketogenesis. CPT inhibitors (e.g., 2-tetradecylglycidyl-CoA and amino- and palmitoylaminocarnitine) decrease blood ketone and blood glucose concentrations in vivo, suggesting that CPT inhibitors can aid in alleviating the diabetic syndrome.

Molecular modeling studies suggest that an eight-membered ring is a better match than a six-membered ring to the putative reaction intermediate for all acyltransferases. The cholinium phosphorus cycles are potential analogs of phosphatidyl choline. The compound shown below shows antimicrobial activity. See CA 109 (19): 170548w, CA 85 (12): 80050j.

Similar compounds have been prepared where R is a shorter chain length and includes aryl and where the group attached to the nitrogen atom is alkyl or phenyl. These compounds have proven to exhibit anticholinesterase activity. See CA 81 (19): 11648j, CA (5): 43448h.

Accordingly, there is a need for more potent inhibitors of all acyltransferases.

DESCRIPTION OF THE PREFERRED EMBODIMENTS

In the compounds of the present invention, the following definitions apply:

A linear or branched chain of 1 to 22 carbon atoms selected from the group consisting of alkyl means straight or branched chain alkyl having 1 to 22 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl (similarly, $C_1$ to $C_6$ alkyl means the above straight or branched alkyl groups having 1 to 6 carbon atoms in the chain).

Alkenyl means straight or branched chain alkenyl having 1 to 22 carbon atoms and at least one double bond and includes 1-propenyl, 1-butenyl, 1-pentenyl, 1-hexenyl, 1-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-eicosenyl, 1-docosenyl, 5,13-docosadienyl, etc.

Alkynyl means a straight or branched chain alkynyl having 1 to 22 carbon atoms and at least one triple bond and includes ethynyl, 1-propynyl, 1-butynyl, 1-pentynyl, 1-hexynyl, 1-heptynyl, 1-octynyl, 1-nonynyl, 1-decynyl, 1-undecynyl, 1-dodecynyl, 1-tridecynyl, 1-tetradecynyl, 1-pentadecynyl, 1-hexadecynyl, 1-heptadecynyl, 1-octadecynyl, 1-nonadecynyl, 1-eicosynyl, 1-docosynyl, 5,13-docosadiynyl, etc.

In the above illustrated alkenyl and alkynyl moieties, only a single point of unsaturation is shown. However, it should be understood that the unsaturated grouping can be at a different position in the carbon chain or include more than one point of unsaturation.

Substituted phenyl means phenyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy isobutoxy, secondary butoxy, tertiary butoxy, pentyloxy, isopentyloxy, hexyloxy, heptyloxy, octyloxy, nonyloxy and decyloxy, haloalkyl which means straight or branched alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Heteroaryl means 5 to 10 membered mono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl.

Substituted heteroaryl means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus.

Alkoxy means straight or branched chain alkoxy having from 1 to 8 carbon atoms and includes methoxy, ethoxy, n-propoxy, isopropoxy, butoxy, isobutoxy, pentyloxy, hexyloxy, heptyloxy, octyloxy, etc.

Haloalkyl means straight or branched chain alkyl having 1 to 10 carbon atoms which is substituted by at least one halogen as mentioned above.

Aminoalkyl means that the alkyl moiety is straight or branched chain alkyl having 1 to 8 carbon atoms and includes, for example, aminomethyl, 2-aminoethyl, 3-aminopropyl, 4-aminobutyl, 6-aminohexyl, 8-aminooctyl, etc.

Substituted benzoyl means benzoyl which is substituted by at least one substituent selected from the group consisting of halogen, amino, nitro, hydroxy, alkyl, alkoxy and haloalkyl on the benzene ring.

The present invention embraces any of racemates and individual optical isomers thereof of the compounds of formula (I) having a chiral carbon atom.

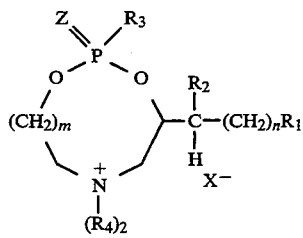

where $R_1$ and $R_3$ are the same or different and are a linear or branched chain of 1 to 22 carbon atoms selected from the group consisting of alkyl, alkenyl or alkynyl, or said $C_1$ to $C_{22}$ chains substituted with halo, $-SR_5$, $-OR_5$, $-NHR_5$, $-NR'_5R_5$ or $-C(O)OR_6$ where $R_6$ is hydrogen or $C_1$ to $C_6$ alkyl;

$R_5$ and $R'_5$ are the same or different and are hydrogen, amino-alkyl substituted with phenyl, substituted phenyl, benzoyl, substituted benzoyl, heteroaryl or substituted heteroaryl;

$R_2$ is hydrogen, $C_1$ to $C_6$ alkyl, phenyl or substituted phenyl;

$R_4$ is hydrogen, $C_1$ to $C_6$ alkyl, phenyl or substituted phenyl;

Z is sulfur or oxygen;

m is an integer from 1 to 3; and n is an integer from 1 to 23.

The compounds of formula (I) are salts (where the counter ion is identified as $X^-$). As such, these salts include pharmaceutically acceptable salts such as where $X^-$ includes the inorganic acid addition salts (e.g., chloride, bromide, hydrochloride, hydrobromide, sulfate, nitrate or phosphate), organic acid addition salts (e.g., acetate, tartrate, citrate, fumarate, maleate, mandelate, oxalate, salicylate, hybenzate, fendizoate, methanesulfonate or p-toluenesulfonate), salts with bases (e.g., salt with triethylamine, diethanolamine, ammonium, guanidine, hydrazine, quinine or cinchonin) or salts with amino acids (e.g., salt with lysine or glutamine).

In the above compounds of formula I, it is preferred that $R_1$ is $C_1$ to $C_{10}$ alkyl substituted with $-CH_3$, m is 1 to 3 and n is 1 to 10. Most preferably, $R_1$ is $C_1$ to $C_5$ alkyl substituted with methyl. Particularly preferred is where R is methylene substituted with methyl, m is 3 and n is 12.

In the case of $R_2$, it is preferred that this substituent is hydrogen or $C_1$ to $C_3$ alkyl; most preferably, hydrogen.

$R_1$ and $R_3$ are the same and are preferably the group $-SR_5$ or $OR_5$. Most preferably, $R_1$ and $R_3$ are $-OR_5$ where $R_5$ is hydrogen or $C_1$ to $C_6$ alkyl. Particularly preferred for $R_5$ groups are hydrogen or methyl.

In the preferred compounds of formula I, it is particularly preferred that Z is oxygen.

In the compounds of formula I, $R_4$ is attached to the nitrogen atom and the remainder of the molecule completes the cationic form of these materials. As such, $R_4$ is preferably hydrogen or $C_1$ to $C_6$ alkyl; most preferably, $C_1$ to $C_3$ alkyl. Particularly preferred for $R_4$ is the group methyl.

As noted above, the anion associated with the cationic species is preferably the chloride or bromide; most preferably, the bromide. It should be understood, however, that the compounds of formula I can be in the free base form. In this free base compound, only a single $R_5$ group is attached to the nitrogen atom.

Especially preferred compounds of formula I are as follows:

6,6-N,N-dimethyl-2-methyl-2-oxo-1,3-dioxa-4-pentadecyl-6-aza-2-phosphacyclooctane bromide;

6,6-N,N-dimethyl-2-fluoro-2-oxo-1,3-dioxa-4-pentadecyl-6-aza-2-phosphacyclooctane bromide;

6,6-N,N-dimethyl-2-hydroxy-2-oxo-1,3-dioxa-4-pentadecyl-6-aza-2-phosphacyclooctane bromide;

6,6-N,N-dimethyl-2-methoxy-2-oxo-1,3-dioxa-4-pentadecyl-6-aza-2-phosphacyclooctane bromide;

6-N-(2-hydroxyethyl)-6-N-methyl-2-methyl-2-oxo-1,3-dioxa-4-pentadecyl-6-aza-2-phosphacyclooctane bromide;

6-N-(2-hydroxyethyl)-6-N-(2-keto-1-hexadecyl)-2-methyl-2-oxo-1,3-dioxa-4-pentadecyl-6-aza-2-phosphacyclooctane bromide; and 6,6-N,N-dimethyl-2-methyl-2-oxo-1,3-dioxa-4-pentadecyl-6-aza-2-thiophosphacyclooctane bromide.

The compounds of formula I of the present invention can be prepared, for example, by the ring-opening reaction of an unsubstituted or alkyl or aryl N-substituted-2-hydroxy-2-substituted morpholine with sodium borohydride (the substituent at position 2 is of the formula $-CH(R_2)(CH_2)_nR_1$ where $R_1$, $R_2$ and n are as previously defined). The ring-opening reaction is well known and has been described in, for example, March Ed., *Advanced Organic Chemistry* incorporated herein by reference. Cleavage at the ring oxygen group produces a tertiary amine (of the morpholine starting material was N-alkyl or N-aryl) where the nitrogen atom is also substituted with 2-hydroxy ethyl and 2-hydroxyethyl further substituted at position 2 with the $-CH(R_2)(CH_2)_nR_1$ group.

The dihydroxy compound formed above can further be reacted with the appropriate phosphonic dichloride or thiophosphones dichloride, i.e., $O=P(Cl_2)R_3$ where $R_3$ is defined above, to produce the free base form of the compounds of formula I.

The salts of the free bases prepared as shown above are easily synthesized by treatment with appropriate alkyl or aryl halide (preferably bromide).

The salts of the compounds of formula I are obtained in the course of the preparation of the compounds of formula I, where $R_4$ is di(alkyl, phenyl or substituted phenyl), by treating the above-mentioned pharmaceutically acceptable acid addition salts with an alkali, a base or an amino acid in a conventional manner. Where one of $R_4$ is hydrogen, the free base is obtained directly. Where $R_4$ is not hydrogen, the compounds typically remain in salt form.

The compounds of formula I of the present invention thus obtained can be separated by employing a conventional separation and purification procedure such as extraction, concentration, neutralization, filtration, recrystallization, column chromatography or thin layer chromatography from the reaction mixture.

The compounds of formula I having an asymmetric carbon are usually formed as racemates. These racemates can be separated into the individual optical isomers by, for example, forming salts with an optically active acid (e.g., mandelic acid, tartaric acid, dibenzoyltartaric acid or 10-camphorsulfonic acid) or an optically active base (e.g., cinchonine, cinchonidine, quinine, quinidine, α-methylbenzylamine or dehydroabiethylamine), or by separating with chromatography or fractional recrystallization. The optically active isomers can also be prepared directly by using optically active starting compounds.

EXAMPLES

General Procedure for the Preparation of Cyclic Phosphino Compounds

Synthesis of N-2-Hydroxyethyl-N-2-hydroxyheptadecyl-N-methyl amine

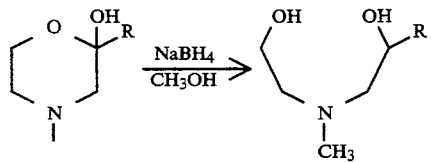

To 2-Hydroxy-4-methyl-2-pentadecylmorpholine (1 g, 3.06 mmol) at 0° C. was added $NaBH_4$ (349 mg, 9.17 mmol) over a period of 10 minutes at 0° C., and the reaction mixture was stirred at 0° C. for 6 hours. Then methanol was removed by rotavap, the residue was taken in ether (100 mL) washed with water (2×25 mL), brine, and dried over sodium sulphate. Evaporation of the solvent gave a pure product. Yield (0.98 g, 97%), NMR $^1H$ (CDCl$_3$, 200 MHz) 0.89 (3H, t, CH$_3$) 1.25 (26H, s, CH$_2$) 1.38 (2H, m. CH$_2$) 2.32 (3H, s, N—CH$_3$) 2.3–2.7 (4H, m, CH$_2$) 3.67 (3H, m, CH$_2$OH, CHOH). NMR $^{13}C$ (CDCl$_3$, 50 MHz) 67.6 64.1, 59.7, 59.3 42.4, 34.9, 31.9, 29.7, 29.3, 25.6, 22.7, 14.1 IR cm$^{-1}$ 3392, 2922, 2853, 1466, 1265, 878, 740.

Synthesis of N-2-Hydroxyethyl-N-2-hydroxyoctadecyl-N-methyl amine

To suspension of 2-Hydroxy-4-methyl-2-hexadecylmorpholine (5 g, 14.66 mmol) in methanol (150 mL) at 0° C. was added $NaBH_4$ (1.1 g, 29 mmol over a period of 10 min. The reaction mixture was brought to room temperature slowly and stirred at room temperature for 12 hours. Additional NnBH$_4$ (200 mg, 5.2 mmol) was added at room temperature and stirred for 2 hours at room temperature. Methanol was removed by rotavop and the residue was treated with water (100 mL) and extracted with CH$_2$Cl$_2$ (3×50 mL). The combined organic phase was washed with water, brine and dried over Na$_2$SO$_4$. Evaporation of the solvent gave a product which was used without further purification in the next step. Yield 4.92g, 98%. NMR $^1H$ (CDCl$_3$, 200 MHz) 0.88 (3H, t, CH$_3$), 1.26 (28H, s, CH$_2$), 1.40 (2H, m, CH$_2$), 2.32 (3H, s, N—CH$_3$), 2.3–2.7 (4H, m, CH$_2$), 3.66 (3H, m, CH2OH, CHOH). NMR $^{13}C$ (CDCl$_3$, 50 MHz) 67.6, 64.2, 59.7, 59.3, 42.5, 34.9, 31.9, 29.6, 29.3, 25.6, 22.6, 14.0. IR (KBr) cm$^{-1}$ 3436, 2918, 2850, 1469, 1087, 880, 722.

Synthesis of (2S 4S, 2R 4R) and (2S 4R, 2R 4S) 2-Methyl-2-oxo-1,3-dioxa-4-pentadecyl-6-aza-6-N-methyl-2-phosphacyclooctane

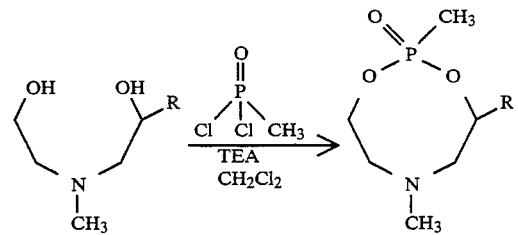

To triethyl amine (0.5 mL, 3.64 mmol) in methylene chloride (200 mL) was added simultaneously, N-2-Hydroxyethyl-N-2-hydroxyheptadecyl-N-methyl amine (300 mg, 0.91 mmol) in methylene chloride (50 mL), methylphosphonic dichloride (121 mg, 0.91 mmol) in methylenechloride (50 mL) over a period of 2 hours. After the addition is over, the reaction mixture was stirred at room temperature overnight. The solvent was removed by rotavap, and the residue was taken in ether (100 mL), the precipitate formed was filtered and discarded. The ether solvent was evaporated by rotavap and the residue was chromatographed on a alumina column eluting with ethyl acetate and hexane (1:1). Two diastereomers were collected. Total yield (49 mg, 14%). First fraction, NMR $^1H$ (CDCL$_3$, 200 MHz); 0.88 (3H, t, CH$_3$), 1.26 (28H, s, CH$_2$), 1.44 (3H, d, J$_{app}$=18 Hz, P—CH$_3$), 2.54 (3H, s, N—CH$_3$), 2.48–3 00 (4H, m, N—CH$_2$), 3.72 (1H, m), 4.26 (1H, m), 4.44(1H, m). $^{13}C$ (CDCl$_3$, 50 MHz); 76.7 (d, J=9.08 Hz), 65.6. (d, J=7.98 Hz) 62.7, 58.7, 42.1, 33.0 (d, J=9.05 Hz) 31.9, 29.7, 29.5, 29.4, 25.4, 22.7, 14.1, 12.4 (d, J=156.38 Hz). 31P (CDCl$_3$, 40 MHz); 26.9. Mass: 388, 374, 280, 278, 266, 250, 192, 152, 138, 123, 110, 96, 82, 70, 58, 43, 29, IR (KBr) cm$^{-1}$ 2917, 2849, 1471, 1232(P=0), 781, 718. Second fraction. (2S 4R, 2R 4S) NMR $^1H$ (CDCl$_3$, 200 MHz); 0.88 (3H, t, CH$_3$), 1.26 (28H, s, CH$_2$), 1.48 (3H, d, J$_{app}$=17.6 HZ, P—CH$_3$), 2.53 (3H, s, N—CH$_3$), 2.5–3.0 (4H, m, N—CH$_2$), 3.88 (1H, m), 4.10 (1H, m), 4.32 (1H, m). $^{13}C$ (CDCl$_3$ 50 MHz); 78.0 (d, J=8.51 HZ), 65.3 (d, J=8.34 Hz), 62.5, 55.8, 45.5, 33.7 (d, J=7.05 Hz), 31.9, 29.7, 29.5, 25.7, 22.7, 14.1, 11.4 (d, J=148.07 Hz). NMR $^{31}P$ (CDCl$_3$, 40 MHZ); 28.1. Mass; 388, 374, 280, 266, 250, 192, 152, 138, 123, 110, 96, 82, 70, 58, 43, 29. IR (KBr) cm$^{-1}$ 2917, 2850, 1473, 1308, 1259(P=O), 1087, 914. 775.

Synthesis of (2S 4S, 2R 4R) and (2S 4R, 2R 4S) 2-Methyl-2-oxo 1,3-dioxa-4-hexadecyl-6-aza-6-N-methyl-2-phosphacyclooctane To triethyl amine (8.7 mL 62.8mmol) in methylene chloride (300 mL) was added simultaneously, N-2-Hydroxyethyl-N-2-hydroxyoctadecyl-N-methyl amine (5.4~, 15.7 mmol) in methylene chloride (125 mL), methylphosphonic dichloride (2.3 g, 17.3 mmol) in methylenechloride (125 mL) over a period of 6 hours. After the addition is over, the reaction mixture was stirred at room temperature overnight. The solvent was removed by rotavop, and the residue was taken in ether (200 mL). The precipitate formed was filtered and discarded. The ether solvent was evaporated by rotavap and the residue was chromatographed on an alumina column. Two diastereomers were collected. First diastereomer was eluted with ethyl acetate and hexane (9:1). Yield 2.42 g. Second diastereomer was eluted with ethylacetate and hexane (1:1). Yield 2.3 g. Total yield, 4.72 g. 75%. First fraction (2S 4S, 2R 4R) NMR $^1$H (CDCl$_3$, 400 MHz); 0.88 (3H, t, terminal CH$_3$), 1.26 (28H, s, CH$_2$), 1.44 (3H, d, J$_{app}$=18 Hz) , 2.54 (3H, s, N—CH$_2$), 2.6–2.5 (1H, m), 2.8 (2H, m), 2.9 (1H, m), 3.75 (1H, m) , 4.25 (1H, m), 4.45 (1H, m). $^{13}$C (CDCl$_3$ 100 MHz); 76.7 (C4), 65.6 (d, J=8.6 Hz, C8), 62.7 (C5), 58.7 (C7), 42.1 (N—CH$_3$), 32.9 (d, J=9.2 Hz), 31.9, 29.6, 29.5, 29.4, 29.3, 25.4, 22.6, 14.1 (terminal CH$_3$), 12.4 (d, J=155.8 Hz, P—CH$_3$). $^{31}$P (CDCl$_3$, 40 MHz), 26.8. Mass; 402, 307, 292, 264, 192, 152, 96, 70, 58. IR (KBr) cm$^{-1}$ 2916, 2849, 1467, 1312, 1233(P=O), 1083, 908, 784. Second fraction (2R 4S, 2S 4R) NMR $^1$H(CDCl$_3$, 400 MHz); 0.88 (3H, t, terminal CH$_3$), 1.26 (28H, s, CH$_2$), 1.6–1.4 (2H, m, CH$_2$), 1.48 (3H, d, J$_{app}$=17.6 Hz), 2.53 (3H, s, N—CH$_3$), 2.8–2.5 (3H, m), 3.05–2.8 (1H, m), 3.9–3.7 (1H, m), 4.23 (1H, m), 4.5–4.3 (1H, m). $^{13}$C (CDCl$_3$ 100 MHz); 77.9 (d, J=8.7 Hz, C4), 65.3 (d, J=7.68 Hz, C8), 62.4 (C5), 55.7 (C7), 45.5 (N—CH$_3$), 33.6 (d, J=7.0 Hz), 31.8, 29.6, 29.5, 29.4, 29.3, 25.6, 22.6, 14.0 (terminal CH$_3$), 11.3 (d, J=148.2 Hz, P—CH$_3$). $^{31}$P (CDCl$_3$, 40 MHZ); 28.0. Mass; 402, 307, 292, 264, 192, 152, 96, 70, 58. IR (KBr) cm$^-$ 2918, 2850, 1471, 1321, 1230(P=O) , 1090, 916, 781.

Synthesis of (2S 4S,2R 4R) 6,6-N,N-Dimethyl-2-methyl-2-oxo-1,3-dioxa-4-pentadecyl-6-aza-2 -phosphacyclooctane bromide

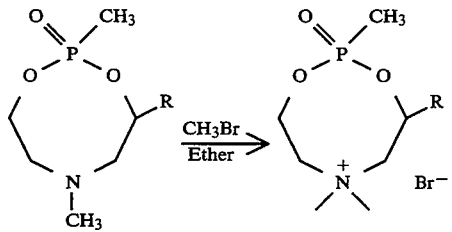

(2S 4S, 2R 4R) 2-Methyl-2-oxo-1,3-dioxa-4-pentadecyl-6-aza-6-N-methyl-2-phosphacyclooctane 150 mg, 0.386 mmol) was taken in ether (15 mL) and CH$_3$Br was bubbled through the reaction mixture for 15 min, and the turbid mixture was stirred at room temperature for 3 days. The solid formed was filtered and washed with ether and recrystallized from CH$_2$Cl$_2$ and methanol. Yield 110 mg, 59%. NMR $^1$H (CDCl$_3$, 400 MHz); 0.88 (3H, t, terminal CH$_3$), 1.26 (26H, CH$_2$ (C$\underline{H}_2$)$_{13}$CH$_3$), 1.66 (3H, d, J$_{app}$=17.9 Hz), P—CH$_3$) 1.8–1.4 (2H, m, C$\underline{H}_2$(CH$_2$)$_{13}$CH$_3$) 3.55 (3H, s, N—CH$_3$), 3.61 (3H, s, N—CH$_3$), 3.85–4.25 (4H, m), 4.5–4.7 (2H, m), 4.92 (1H, m). $^{13}$C (CDCl$_3$, 100 MHz); 70.3, 69.9 (d, J=7.56 Hz), 63.6, 60.7, (d, J=7.0 Hz), 57.1, 51.1, 34.6 (d, J=6.0 Hz), 31.8, 29.6, 29.5, 29.2, 24.8, 22.5, 14.0, 10.7 (d, J=143.6 Hz). $^{31}$P (CDCl$_3$, 162 MHz); 32.9 Mass (FAB in glycerol); 404.5 (cation). IR (KBr) cm$^-$ 2917, 2849, 1471, 1312, 1232(P=O), 99, 719.

Synthesis of (2S 4R, 2R 4S) 6,6-N,N-Dimethyl-2-methyl-2-oxo-1, 3-dioxa-4-pentadecyl-6 -aza-2 -phosphacyclooctane bromide (2S 4R, 2R 4S) 2-Methyl 2-oxo-1,3-dioxa-4-pentadecyl-6-aza-6- N-methyl-2-phosphacyclooctane (100 mg, 0.257) was taken in ether (10 mL) and CH$_3$Br was bubbled through the reaction mixture for 15 min, and the reaction mixture was stirred at room temperature for a week. The solid formed was filtered and washed with ether and recrystallized with CH$_2$Cl$_2$ and MeOH. Yield 100 mg, 80%. (2S 4R, 2R 4S) NMR $^1$H (CDCl$_2$, 400 MHz); 0.88 (3H, t, (CH$_2$)CH$_3$), 1.25 (24H, (C$\underline{H}_2$)$_{12}$CH$_3$), 1.3–1.5 (2H, m, (CH$_2$)$_{12}$C$\underline{H}_3$), 1.64 (3H, d, J$_{app}$=17.5 Hz, P—CH$_3$), 1.65–1.85 (2H, m, (C$\underline{H}_2$)$_{13}$CH$_3$), 3.74 (3H, s, N—CH$_3$), 3.75 (3H, s, N—CH$_3$), 3.7–3.85 (1H, m), 4.2–4.35 (3H, m), 4.5–4.75 (3H, m). $^{13}$C (CDCl$_3$, 100 MHz); 73.1 (d, J=7.58 Hz), 71.1. 63.6. 59.8 (d, J=7.13 Hz), 58.4, 49.4, 33.8, 31.9, 29.7, 29.6, 29.5, 29.3, 29.26, 25.2, 22.7, 14.1, 10.8 (d, J=141.5 Hz). $^{31}$P (CDCl$_3$, 162 MHz); 31.7. Mass (FAB in glycerol); 404.5 (cation). IR (KBr) cm$^-$ 2916, 2849, 1471, 1320, 1231(P=O), 990.

Synthesis of (2S 4S, 2R 4R) 6,6-N,N-Dimethyl-2-methyl-2-oxo-1,3-diox-4-hexadecyl-6-aza-2-phosphacyclooctane bromide (2S 4S, 2R 4R) 2-Methyl-oxo-1,3 dioxa-4-hexadecyl-6-aza-6-N-methyl-2-phosphacyclooctane (1 g 2.4 mmol) was taken in ether (25 mL) and CH$_3$Br was bubbled through the reaction mixture for 30 min and the reacting mixture was stirred at room temperature for a week. The solid formed was filtered and washed with ether. Combined ether solution was again bubbled with CH$_3$Br for 30 min and stirred at room temperature for an additional week. The solid formed was filtered and washed with ether. The combined solid was recrystallized from CH$_2$Cl$_2$. Yield 930 mg 75%. NMR $^1$H (CDCl$_3$, 400 MHz); 0.88 (3H, t, (CH$_2$)$_{14}$,CH$_3$), 1.26 (26H, s, (CH$_2$)$_{13}$,CH$_3$), 1.45 (2H, m, (C$\underline{H}_2$)$_{13}$,C$\underline{H}_3$), 1.62 (3H, d, J$_{app}$-18 Hz, P—CH$_3$), 1.72 (2H, m, (CH$_2$)$_{14}$,CH$_3$), 3.67 (3H, s, N—(CH$_3$), 3.82 (3H, s, N—CH$_3$), 3.85–4.95 (1H, m), 4.15–4.3 (2H, m), 4.35–4.55 (2H, m), 4.65 (1H, m), 4.85 (1H, m). $^{13}$C (CDCl$_3$, 100 MHz); 70.9, 69.3 (d, J=7.9 Hz), 64.0, 60.2 (d, J=7.33 Hz), 56.6 (N—CH$_3$), 50.9 (N—CH$_3$), 34.8 (d, J=6.9 Hz), 31.8, 29.6, 29.5, 29.4, 29.2, 29.0, 24.8. 22.6, 14.0 (terminal CH$_3$), 10.8 (d, J=145 Hz, P—CH$_3$). $^{31}$P (CDCl$_3$, 40 MHz); 33.6. Mass (FAB in NBA); 418.5 (cation). IR (KBr) cm$^-$ 2920, 2850, 1469, 1318, 1246(P=0), 1077, 919, 8.06. Anal. calculated for C$_{23}$H$_{49}$NO$_3$PBr: C, 55.41; H, 9.91; N, 2.81. Found: C, 55.16; H, 10.04; N, 2.73.

Synthesis of (2S 4R, 2R 4S) 6,6-N,N-Dimethyl-2-methyl-2-oxo-1,3-dioxa-4 hexadecyl-6-aza-2-phosphacyclooctane bromide.

(2S 4R, 2R 4S) 2-Methyl-2-oxo-1,3-dioxa-4-hexadecyl-6-aza-6 N-methyl-2-phosphacyclooctane (1 g, 2.48 mmol) was taken in ether (25 mL) and CH$_3$Br was bubbled through the reaction mixture for 30 min and the resulting solution was stirred at room temperature for a week. The solid formed was filtered and washed with ether and recrystallized from CH$_2$Cl$_2$ and MeOH. Yield 1.1 g, 89% NMR 1H (CDCl$_3$, 400 MHz); 0.88 (3H, t, (CH$_2$)CH$_3$), 1.25 (26H, (CH$_2$)$_{13}$,CH$_3$), 1.37–1.5 (2H, m, CH$_2$(CH$_2$)$_{13}$,CH$_3$), 1.64 (3H, d, J$_{app}$-17.6 Hz, P—CH$_3$), 1.65–1.85 (2H. m, CH$_2$(CH$_2$)$_{14}$,CH$_3$), 3.74 (3H, s, N—CH$_3$), 3.77 (3H, s, N—CH), 3.6–3.85 (IH, m), 4.2–4.35 (3H, m), 4.5–4.75 (3H, m). $^{13}$C 100 MHz); 73.1 (d, J=7.28 Hz), 63.4, 59.8 (d, J=6.4 Hz), 58.4 (N—CH$_3$), 49.1 (N—CH$_3$), 33.7 (d, J=2.93 Hz), 31.8, 29.6, 29.4, 29.2, 25.1, 22.6, 14.0 (terminal CH$_3$), 10.8 (d, J=140.9 Hz, P—CH$_3$). $^{31}$P (CDCl$_3$, 40 MHz); 38.1. Mass (FAB in NBA), 418.5 cation). IR (KBr) cm$^{-1}$ 2917. 2849, 1472, 1321, 1231(P=O), 1091, 990. Anal. Calculated for C$_{23}$H$_{49}$NO$_3$PBrH$_2$O: C, 53.48; H, 9.95; N, 2.71. Found: C, 53.11; H, 9.75; N, 2.74.

PHARMACOLOGICAL EXAMPLES

The following are the results pharmacological experiments exhibiting the effectiveness of the compounds (I), or their salts, of the present invention.

PKC INHIBITION

Methods

Compounds were assayed for the inhibition of protein kinase C using the methods of G. Kumaravel, C. L. Ashendel, and R. D. Gandour (1993) *J. Med. Chem.*, 35, 177–178, with slight modifications. Instead of rat brain PKC, we used a mixture (1:1) of recombinant PKC alpha and beta-2 (prepared by expression in insect cells and partially purified). The compounds were assayed in methanol and the concentration ranged from 160–0.016 μg/ml (5 values). Listed below are the IC-50 values.

P16CBr-I=(2S 4S, 2R 4R) 6,6-N,N-Dimethyl-2-methyl-2-oxo-1,3-dioxa-4-hexadecyl-6-aza-2-phosphacyclooctane bromide.

P16CBr-II=(2S 4R, 2R 4S) 6,6-N,N-Dimethyl-2-methyl-2-oxo-1,3-dioxa-4-hexadecyl-6-aza-2-phosphacyclooctane bromide.

| Compound | IC-50 |
|---|---|
| P16CBr-I | 4.8 μM |
| P16CBr-II | 9.9 μM |

The compounds of formula I are also inhibitors of those biological functions where a lipid and a choline structure are required for activity. They are also surfactant biocides, inhibitors of protein kinase C, and male contraceptives.

When the compounds of the present invention or the pharmaceutically acceptable salts thereof are used as drugs, they can be orally or parenterally administered alone or in the form of powder, granules, tablets inclusive of film-coated tablets and sugar coated tablets, capsules, injections, drip infusions, suppositories, ointments, cataplasms or eye drops prepared by admixing with pharmaceutically acceptable carriers, vehicles or diluents to patients in need of therapy. The dose may vary depending upon the disease to be treated, the conditions of patient, the age of patient or way of administration, and in case of oral administration, the daily does for human adults ranges from 1 to 1,000 mg, preferably from 50 to 500 mg, in one to several times divided doses.

We claim:

1. An optically active or racemic mixture of a compound of the formula:

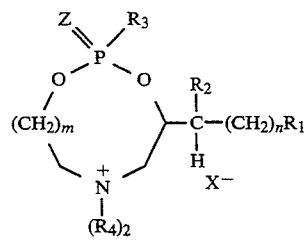

where R$_1$ and R$_3$ are the same or different and are halo or a linear or branched chain of 1 to 22 carbon atoms selected from the group consisting of alkyl, alkenyl; and alkynyl; said C$_1$ to C$_{22}$ chain is optionally substituted with halo, —SR$_5$, —OR$_5$, —NHR$_5$, —NR$_5$·R$_5$ or —C(O)OR$_6$ where R$_6$ is hydrogen or C$_1$ to C$_6$ alkyl;

R$_5$ and R$_5'$ are the same or different and are hydrogen; amino-alkyl substituted with phenyl, substituted phenyl, benzoyl, substituted benzoyl, heteroaryl or substituted heteroaryl;

R$_2$ is hydrogen, C$_1$ to C$_6$ alkyl, phenyl or substituted phenyl;

R$_4$ is hydrogen, C$_1$ to C$_6$ alkyl, phenyl or substituted phenyl;

Z is sulfur or oxygen;

m is an integer from 1 to 3;

n is an integer from 1 to 23; and

X is a pharmaceutically acceptable counter ion.

2. The compound of claim 1 wherein m is 1 and Z is oxygen.

3. The compound of claim 2 wherein R$_2$ is hydrogen.

4. The compound of claim 2 wherein R$_1$ is C$_1$ to C$_{20}$ alkyl substituted with CH$_3$.

5. The compound of claim 3 wherein n is an integer of from 1 to 14.

6. The compound of claim 4 wherein R$_3$ is C$_1$ to C$_6$ alkyl.

7. The compound of claim 6 wherein R$_2$ is hydrogen, C$_1$ to C$_6$ alkyl or phenyl.

8. The compound of claim 7 wherein R$_4$ is hydrogen.

9. The compound of claim 7 wherein R$_4$ is hydrogen or C$_1$ to C$_6$ alkyl.

10. The compound of claim 9 wherein R$_4$ is C$_1$ to C$_3$ alkyl.

11. The compound of claim 10 wherein X is a pharmaceutically acceptable inorganic acid addition salt.

12. A method for inhibiting the enzyme protein kinase C in mammals comprising treating said mammals with an effective amount of a compound of the formula:

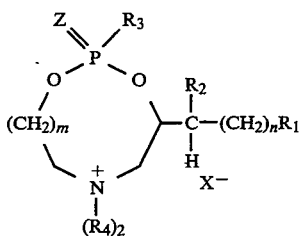

where $R_1$ and $R_3$ are the same or different and are halo or a linear or branched chain of 1 to 22 carbon atoms selected from the group consisting of alkyl; alkenyl; and alkynyl; said $C_1$ to $C_{22}$ chain is optionally substituted with halo, $-SR_5$, $-OR_5$, $-NHR_5$, $-NR'_{5'}R_5$ or $-C(O)OR_6$ where $R_6$ is hydrogen or $C_1$ to $C_6$ alkyl;

$R_5$ and $R_{5'}$ are the same or different and are hydrogen; amino-alkyl substituted with phenyl, substituted phenyl, benzoyl, substituted benzoyl, heteroaryl or substituted heteroaryl;

$R_2$ is hydrogen, $C_1$ to $C_6$ alkyl, phenyl or substituted phenyl;

$R_4$ is hydrogen, $C_1$ to $C_6$ alkyl, phenyl or substituted phenyl;

Z is sulfur or oxygen;

m is an integer from 1 to 3; and

X is a pharmaceutically acceptable counter ion.

n is an integer from 1 to 23.

13. The method of claim 12 wherein m is 1 and Z is oxygen.

14. The method of claim 13 wherein $R_2$ is hydrogen.

15. The method of claim 13 wherein $R_1$ is $C_1$ to $C_{20}$ alkyl substituted with $CH_3$.

16. The method of claim 14 wherein n is an integer of from 1 to 14.

17. The method of claim 15 wherein $R_3$ is $C_1$ to $C_6$ alkyl.

18. The method of claim 17 wherein $R_2$ is hydrogen, $C_1$ to $C_6$ alkyl or phenyl.

19. The method of claim 18 wherein $R_2$ is hydrogen.

20. The method of claim 17 wherein $R_4$ is hydrogen or $C_1$ to $C_6$ alkyl.

21. The method of claim 18 wherein $R_4$ is $C_1$ to $C_3$ alkyl.

22. The method of claim 21 wherein X is a pharmaceutically acceptable inorganic acid addition salt.

* * * * *